United States Patent [19]

Nagasaki et al.

[11] Patent Number: 4,631,582

[45] Date of Patent: Dec. 23, 1986

[54] ENDOSCOPE USING SOLID STATE IMAGE PICK-UP DEVICE

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 766,311

[22] Filed: Aug. 16, 1985

[30] Foreign Application Priority Data

Aug. 31, 1984 [JP] Japan .................... 59-183089

[51] Int. Cl.$^4$ .................... A61B 1/04; A61B 1/06
[52] U.S. Cl. .................... 358/98; 128/6; 358/42; 358/168; 358/174; 358/176
[58] Field of Search .................... 358/98, 42, 39, 41, 358/161, 163, 164, 168, 169, 170, 174, 176, 179; 128/6–9, 11, 13

[56] References Cited

U.S. PATENT DOCUMENTS

| 4,532,918 | 8/1985 | Wheeler | 128/6 |
| 4,535,758 | 8/1985 | Longacre | 358/168 |
| 4,546,379 | 10/1985 | Sarofeen | 358/42 |
| 4,562,831 | 1/1986 | Murakoshi | 358/98 |

FOREIGN PATENT DOCUMENTS 65962 6/1976 Japan .
54933 4/1980 Japan .

*Primary Examiner*—Howard W. Britton
*Attorney, Agent, or Firm*—Armstrong, Nikaido, Marmelstein & Kubovcik

[57] ABSTRACT

An endoscope is disclosed having a solid state image pick-up for receiving an image from a subject to be examined. The endoscope includes an illuminating source for projecting light onto the subject, a first level detector for detecting a level of a video signal supplied from the solid state image pick-up device, a first level comparator connected to the first level detector for comparing the level of the signal detected by the first level detector with a preset first reference level and generating a first control signal in accordance with the level difference, and a light controller connected to the output of the first level comparator for controlling the amount of light emitted from the illuminating source based on the first control signal. The endoscope also includes a gain-variable amplifier for receiving and amplifying the video signal from the solid state image pick-up device, a second level detector connected to the gain-variable amplifier for detecting the level of the signal therefrom, and a circuit connected to the second level detector for comparing the level of the signal detected by the second level detector with a preset second reference level and generating a second control signal in accordance with the level difference therebetween and providing the second control signal as a gain controlling signal to the gain-variable amplifier.

7 Claims, 3 Drawing Figures

ENDOSCOPE USING SOLID STATE IMAGE PICK-UP DEVICE

BACKGROUND OF THE INVENTION

This invention relates to an endoscope using a solid state image pick-up device, wherein the dynamic range of the signals obtained by said device is controlled by both the illuminating means and a gain-variable amplifying means. The control by the illuminating means is supplemented by the gain-variable amplifying means.

Recently, various endoscopes using a solid stare image pick-up device such as CCD (charge coupled device) have been proposed. In such endoscopes, when the color imaging method uses a single CCD, a method of providing a color filter separately or in one piece with the CCD and a method to sequentially switch the light of 3 primary colors and project it onto the CCD have been contemplated. The detailed configurations of such methods are described, for example, in Japan Parent Journal Nos. 55-54933 and 51-65952.

A CCD includes many photosensitive picture elements called picture cells as described in an article in "Scientific American" published in February 1974. The picture cells are arranged perpendicular to the wide angle center latitude of the object lens system to form a rectangular grid pattern as a whole. If such grid pattern surface is used as a light receiving surface and light energy is incident on the light receiving surface, the electrons existing within each picture cell region are accumulated or gathered to form a lump of charges. After a specific time, these charges are moved to an electrode corresponding to each picture cell and an output signal proportional to the size of the charge lump is produced. Therefore, the lump of charges for part of a received image with low brightness is small, and that for a part of the image with a high brightness is large.

The sensitivity and dynamic range of the CCD are important characteristics to be considered in the present application. The sensitivity of the CCD is the ability to accumulate the signal charges which correspond to the quantity of incident light. On the other hand, the CCD contains noise charges caused by dark current and smearing. Therefore, the signal charges for the part of the received image with low brightness are buried under the noise charges, resulting in an unclear picture image. The dynamic range of the CCD is determined by the amount of the noise charges.

Some unclear picture images which are displayed are attributable to the spectral luminous efficiency. That is, in a method in which 3 primary color light are used, the received image formed by the same brightness decreases in brightness on the display screen in the following descending order: green, red, blue. Therefore, in an endoscope using this method, accurate level control cannot be expected if the control is made in accordance with the brightness level of the 3 primary color signals. That is, it is necessary to change the control sensitivity in the order of blue, red and green.

As an example of an endoscope which addresses the aforementioned problems, the one shown in FIG. 1, is known in the art. The endoscope shown in FIG. 1 uses a color imaging method with a color filter.

In FIG. 1, the entire endoscope is indicated by reference numeral 1, and in the rigid front end portion of the inserting part 2 an imaging means is provided.

That is, at the opening formed in the front end portion, an object lens 3 is positioned to form an image at a specified focal plane. CCD 4 is positioned such that its imaging surface (light receiving surface) is positioned at the focal plane of said object lens 3.

An analyzer (polarizer) 5 is positioned in the optical path between object lens 3 and CCD 4, for example, at the pupil position of object lens 3. Thus, the reflected light from a subject is incident on the imaging surface through analyzer 5. Analyzer 5 can be rotated through an angular range of about 90 degrees by a driver 6.

The subject image formed on the aforementioned imaging surface is converted into video signals and input to TV signal converter 7. The video signals are then converted into 3 RGB color TV signals by TV signal converter 7 and applied to the RGB terminals of the color TV monitor 8 for display.

In addition to the aforementioned imaging means, the inserting part 2 includes an illuminating means. A light guide 9 is formed of an optical fiber bundle, the rear end of which is detachably connected to a light source device 10. Light source device 10 has an illuminating lamp 11 for emitting light which is reflected by the concave surface of a reflecting mirror 12 and condensed by a condenser 13 to be projected onto the rear end of light guide 9.

The illuminating light condensed by condenser 13 passes through light guide 9, and is emitted at the front end face of the light guide 9. The light is then projected onto a light distributing lens 14 and expanded.

A polarizer 15 is positioned at a converged position of the light distributing lens 14, between the light distributing lens 14 and the front end face of the light guide 9, to polarize the illuminating light projected from the front end face of the light guide 9 into a polarized wave (e.g. P wave).

Polarizer 15 disposed on the side of the illuminating means and analyzer 5 on the side of the imaging means form a portion of the means for changing the quantity of illuminating light by detecting the output signal level according to the change of the quantity of illuminating light and adjusting analyzer 5 accordingly.

The video signal output from the CCD 4 is applied to one input of comparator 17. The other input of comparator 7 receives a voltage level set at a reference level Vs such as a saturation level. When the video signal is higher than the reference level Vs, a high level signal is output from comparator 17. The output of the comparator 17 is integrated for a 1 frame period by integrator 18 and the integrated value is then amplified by the amplifier 19 and subtracted from a level Vo where the integrated value corresponds to 0 by subtracter 20 to control the driver 6. Thus a regression circuit is formed.

The driving force of the driver 6 is changed in accordance with the control signal (driving signal) level input through subtracter 20. For example, as in a moving coil-type voltmeter, if the input signal level is high, the driving force is increased against a helical spring, etc., an initializing force, and the analyzer 5 is installed on its rotating shaft (which is set to pass only the P wave component when not rotated) is rotated through an angle in accordance with the level of the control signal.

On the front surface of the imaging surface of CCD 4, a 3 primary color filter of, for example, the mosaic type is provided. The light receiving elements of the imaging surface receive light which corresponds to the picture elements of each wavelength of the 3 primary colors. The picture elements are separated into each primary color signal by the sample hold circuit within the TV signal converter 7. After the horizontal synchronizing signal and vertical synchronizing signal are superimposed, they are output as RGB color signals.

In the example shown in FIG. 1, the driver 6 is driven by the control signal from the regression circuit to change the rotational angle of analyzer 5. In accordance with the rotational angle of analyzer 5, the quantity of light incident on the imaging surface can be controlled.

In the aforementioned example, however, the quantity of light incident on CCD 4 is simply decreased or increased in accordance with the change of the output signal level. It does not provide such a control in which uniformly clear picture images can be obtained from a small quantity of light or a large quantity of light. Although, it may prevent, to some extent, the dynamic range from decreasing.

The aforementioned example also has a disadvantage in that it takes a long time from when then output signal level is changed to the time when the analyzer 5 is rotated in the specified angle.

Furthermore, in a conventional endoscope, the quantity of light is adjusted by manually switching the ND (neutral density) filter inserted in the beam in the light source device. Therefore, it also lacks the quick response and has the disadvantage that the light quantity adjustment can only be made in several stages.

SUMMARY OF THE INVENTION

An object of this invention is to provide an endoscope using a solid state image pick-up device which can correct the dynamic range so that uniformly clear picture images can be displayed from a small quantity of light or from a large quantity of light.

Another object of this invention is to provide an endoscope using a solid state image pick-up device which can provide quick response and high speed control.

A further object of this invention is to provide an endoscope using a solid state image pick-up device which uses both light adjusting means and electrical control means, and supplements the control by the light adjusting means with the electrical control means instead of only the simultaneous functioning of them.

The endoscope of the present invention includes a light adjusting means for detecting the output level of the signal obtained by the solid state image pick-up device and adjusts the light from the illuminating light source on basis of the detected level, a gain-variable amplifying means for amplifying the signal at the detecting end of said means, and a means for detecting the signal coming from the amplifying means and for controlling the gain of said amplifying means on basis of the detected level.

BRIEF DESCRIPTION OF THE DRAWINGS

The above described invention will be further described in the following detailed description, wherein.

DETAILED DESCRIPTION OF PREFERRED EMBODIMENT

The following will describe the present invention using the illustrated embodiment.

Figure 2:
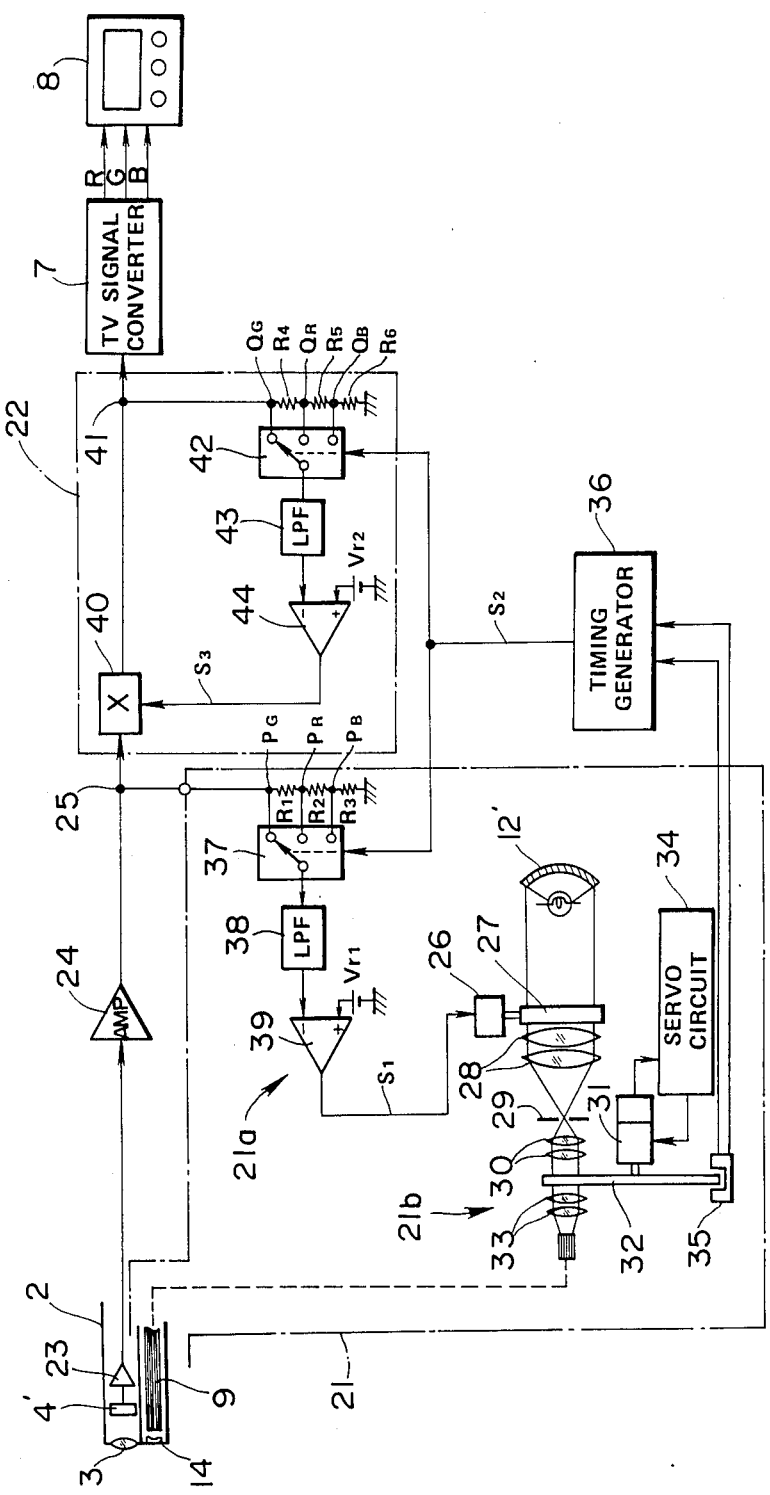
FIG. 2 is a block diagram of one embodiment of a device in accordance with the instant invention.
Figure 3:
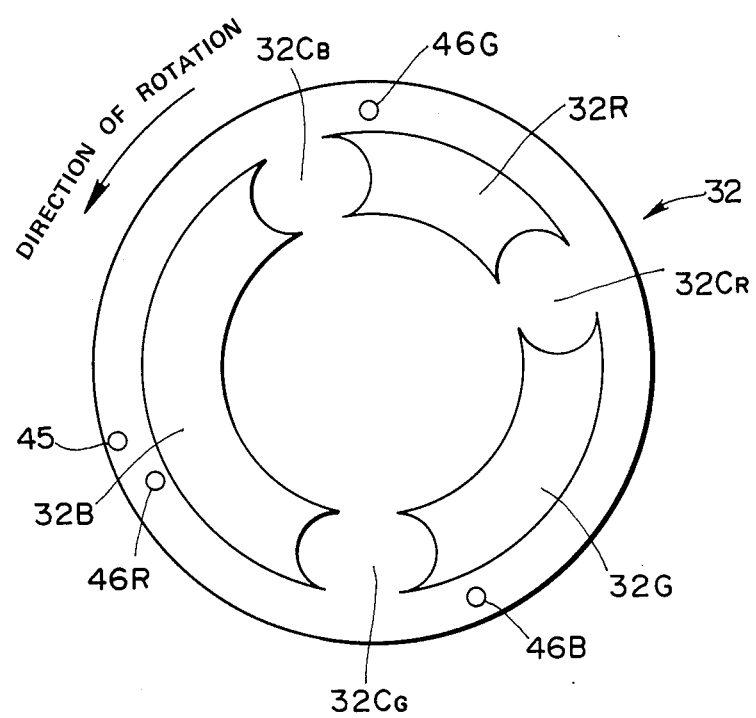
FIG. 3 is a front view of a rotary filter used in the endoscope of FIG. 2.

FIG. 2 is a block diagram of an endoscope related to a first embodiment of this invention and FIG. 3 is a front view of a rotary filter used in the embodiment of FIG. 2.

Figure 1:
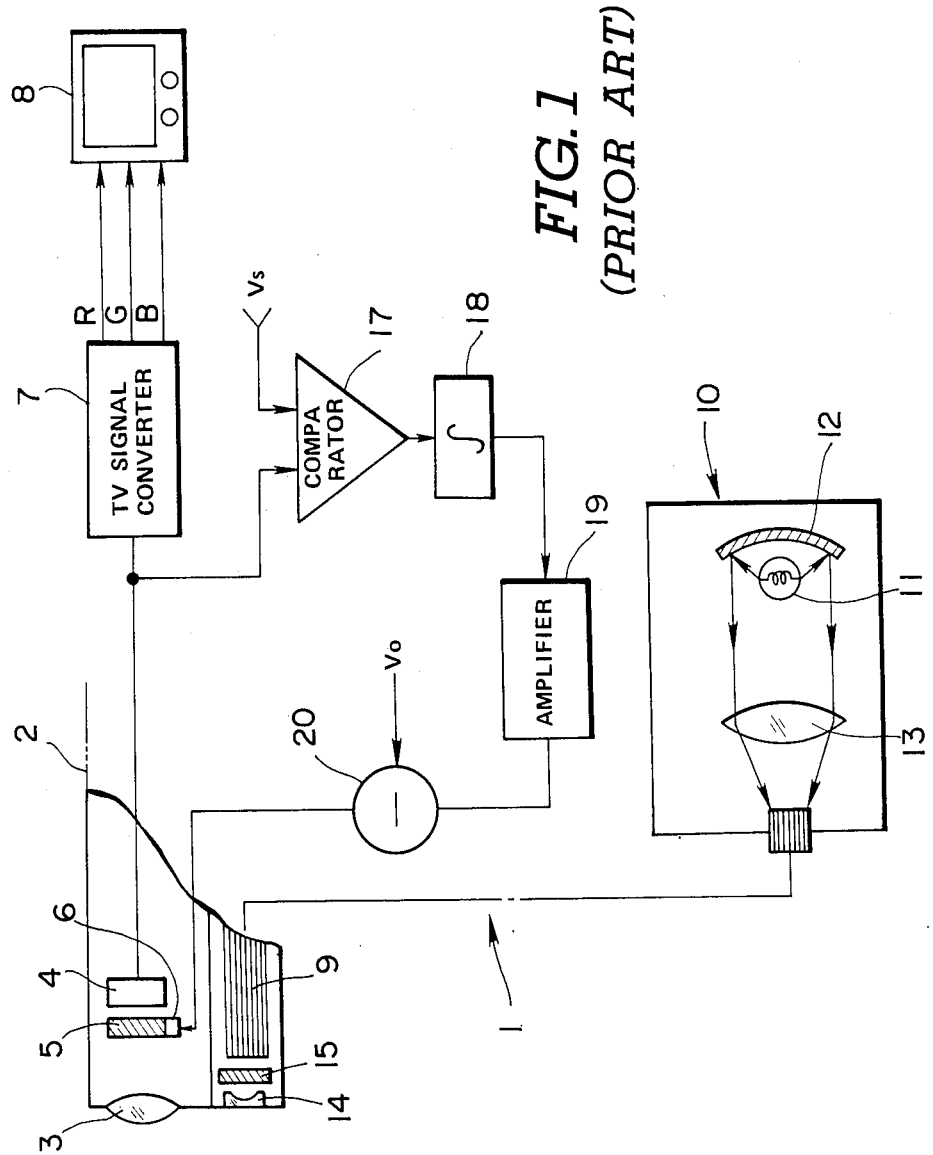
FIG. 1 is a block diagram showing an example of a conventional endoscope.

In FIG. 2, the same symbols are used for similar parts as in FIG. 1. This embodiment consists of an illuminating means 21 which illuminates a subject to be observed and has a light adjusting function and a gain control means 22 which controls the amplitude of the signal obtained by a solid state image pick-up device such as CCD 4'.

That is, the signal from the CCD 4' provided at the front end of inserting part 2 of the endoscope is introduced to the first signal detecting point 25 for automatic light adjusting of the illuminating means 21. This is accomplished via the preamplifier 23 and video amplifier 24 connected in series and at the same time the output therefrom is supplied to the gain controlling means 22 connected behind the first detecting point 25.

Illuminating means 21 consists of circuit section 21a and optical section 21b. Circuit section 21a produces a light control signal S1, formed on basis of the signal from the first detecting point 25, to drive galvanometer 26 of optical section 21b. The output shaft of galvanometer 26 is connected to diaphragm 27 which adjusts illuminating light from the light source section 12. The illuminating light from light source section 12' is then projected into condenser system 28. The light passing through the condenser system 28 is condensed at slit 29. The light is then incident on the inlet side transfer lens system 30 provided behind the slit 29 which transforms the illuminating light into a specific width. The illuminating light passes through a 3-color rotary filter 32 and then is incident on the outlet side transfer lens system 33. Rotary filter 32 is rotated by means of the synchronous motor 31. The output light is thus introduced to the inlet end of light guide fiber 9. Synchronous motor 31 has a servo circuit 34 and rotates rotary filter 32 at a fixed speed in a fixed direction. Rotation detector 35 detects a start pulse to indicate the rotation start position and the light shielding portion for reading R, G and B of rotary filter 32 and the read pulse to indicate the read start position from the CCD. The signals detected by the detector 35 are supplied to timing generator 36 to thus control it.

Circuit section 21a of the illuminating means 21 supplies signals from the first detecting end 25 to one end of the 3 series resistances R1, R2 and R3. The series resistances R1, R2 and R3 are connected to ground at the other end thereof. Intersections $P_G$, $P_R$ and $P_B$ are supplied to 3-input analog switch 37. The signal level of $P_G$, $P_R$ and $P_B$ supplied to the analog switch 37 is set at such level as to meet the spectral luminous efficiency of the green light, red light and blue light in that order, so independent light adjustment can be made during each color signal period. That is, the timing generator 36, which receives the pulse detected by the rotation detector 35, generates the switching pulse S2 for each of R, G and B in accordance with the aforementioned start pulse and read pulse. The switching pulse also sets the position of analog switch 37.

The output of the analog switch 37, as switched for each color signal period, is supplied to the first input of first comparator amplifier 39 via low pass filter 38. A reference voltage source, supplying a voltage Vr1 corresponding to the average value of the minimum limit allowable for the dynamic range of the CCD output signals, is supplied to the second input of the first comparator amplifier 39. When the average value (brightness signal) of the signal from analog switch 37 becomes lower than Vr1 during each color signal period, the first comparator amplifier 39 applies the light control signal S1 to galvanometer 26.

In gain controlling means 22, the signal at the first detecting point 25 is received by multiplier 40 whose output is then introduced to second detecting point 41. The signal at the second detecting point 41 is supplied to color monitor 41 via TV signal converter 7 and displayed, and is also supplied to one end of the series circuit consisting of resistances R4, R5 and R6. The other end of the above series circuit is connected to ground. The signals at intersections $Q_G$, $Q_R$ and $Q_B$ are supplied to analog switch 42. The same switching pulse S2 as that for the analog switch 37 of the illuminating means 21 is applied to analog switch 42. The signal selected by analog switch 42 is supplied to the first input of second comparator amplifier 44. A reference voltage source Vr2 is connected to the second input of second comparator amplifier 44. Vr2 is set at a voltage corresponding to the brightness signal level of the minimum limit to allow the dynamic range of the signal come through a multiplier 40, i.e., the controlled signal, and when the level of the signal from low pass filter 43 becomes lower than Vr2, the gain of multiplier 40 can be controlled.

FIG. 3 shows the aforementioned rotary filter 32, with filter parts 32B, 32G and 32R for transmitting the blue light, green light and red light of the white light from the light source section 12', respectively. Between the filter parts are light shielding parts $32C_B$, $32C_G$ and $32C_R$, which create the light shielding period between the periods when a primary color light is emitted by rotating the filter one turn during sequential field periods. Hole 45 detects the start pulse of the rotary filter 32 and symbols 46R, 46G and 46B are holes to detect the read pulses for R, G and B video signal reading. The start pulse occurs when each field period starts.

In the endoscope thus formed, the illuminating light for which the shielding periods and 3 primary color light periods are set by the rotary filter 32 passes through the outlet side transfer lens 33, light guide fiber 9 and light distributing lens 14 and illuminates a subject. The reflected light from the subject corresponding to the repetition of each period is incident upon the light receiving surface of the CCD 4'. The video signals read from the CCD 4' are introduced to second detecting point 25 via preamplifier 23 and video amplifier 24 and a part of it is introduced into the multiplier 40 and another part into the series resistances R1, R2 and R3 on the side of illuminating means 21.

For example, during the red signal period, the analog switch 37 supplies the red signal of the divided level set at the intersection $P_R$ of the resistances R1 and R2 to the following low pass filter 38 which then applies the average value of the signals to the first input of the first comparator amplifier 39. When said average value is smaller than the reference voltage VR1, first comparator amplifier 39 issues the light controlling signal S1 to have the galvanometer 26 increase the opening of diaphragm 27. This increases the quantity of illuminating light from light source part 12' and the light energy reaching the CCD 4' and thus the brightness level of the video signal. As a result, the amplitude of the red signal increases and the dynamic range can be increased. The first comparator amplifier 39 also controls the diaphragm 27 by outputting a light controlling signal proportional to the level difference between the Vr1 and output level of low pass filter 38.

In the present invention the light control in illuminating means 21 is accomplished by using an independent signal level for each primary color signal. That is, the signal level of Point $P_R$ during the red signal period, the level of Point $P_G$ during the green signal period, and the level of Point $P_B$ during the blue signal period are used as the signal to be compared by first comparator amplifier 39. For this reason, the blue signal with the weakest spectral luminous efficiency can be controlled on basis of the signal of the smallest level at Point $P_B$, and its light controlling rate is higher than for the red signal period and green signal period. During the green signal period with the strongest spectral luminous efficiency, the light control occurs with a larger decrease in the brightness level than for the red signal and blue signal.

In the present invention, the signals for which the above light control occurs can be further gain-controlled electrically at a high speed. In the illuminating means 21, even if the light controlling signal S1 is output by the first comparator amplifier 39 when the signal level at first detecting point 25 becomes lower, it takes a considerable time until the diaphragm 27 widens the opening. In the meantime, the CCD 4' reads the signals from the illuminating light with insufficient brightness and supplies an output to the multiplier 40. Therefore, in the present invention, the signals at second detecting point 41 which come from the multiplier 40 are formed at Points $Q_G$, $Q_R$ and $Q_B$ at specified divided levels and input to the analog switch 42 in accordance with each signal period. The analog switch 42 is operated by the switching pulse S2 in synchronization with analog switch 37 on the side of illuminating means 21 to supply selected signals to low pass filter 43. The second comparator amplifier 44 issues the gain controlling signal S3 proportional to the level difference between the average value of the signals formed by low pass filter 43 and Vr2 and can immediately control the multiplier 40. This controlling speed is much faster than the operating speed of galvanometer 26 and diaphragm 27 and therefore, the video signal level can be raised before the light control occurs.

Since the present invention uses a gain controlling means 22 to control the video signal after the light control occurs, when the dynamic range is narrow because the signal level cannot be raised sufficiently by the light control only, further control can be made by means of the gain controlling means 22. Generally the method to control the circuit gain is superior in the signal-to-noise ratio (SN ratio) to the method of adjusting the illuminating light, and therefore, the SN ratio is improved more than when the light control and gain control are made in parallel. As a result, the priority is placed on the gain control rather than on the light control.

Thus the present invention can provide a picture image with a wide dynamic range and in conformity with the spectral luminous efficiency.

In addition to the light controlling means consisting of the aforementioned galvanometer 26 and diaphragm 27, the quantity of illuminating light can be controlled by using the polaroid filter as described in FIG. 1 or combination of the polaroid filter and liquid crystal. Since this invention is characterized in that the light controlling means and gain controlling means are combined in series, it can also be applied to an endoscope using a color mosaic filter as shown in FIG. 1.

As explained above, since this invention adopts the electrical gain control in addition to the illuminating light control as a means to control the output signals of the solid state image pick-up device, the slow response speed of the mechanical driving section of the light controlling means can be compensated for by the gain controlling means. Also when a sufficient dynamic range cannot be obtained by the light controlling means only, the control can be made by the gain controlling means, thus making it possible to obtain the video signals with a good SN ratio.

It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. An endoscope with a solid state image pick-up for receiving an image from a subject to be examined, comprising:
an illuminating means for projecting light onto the subject;
a first level detecting means for detecting a level of a video signal supplied from the solid state image pick-up device;
a first level comparing means connected to said first level detecting means for comparing the level of the signal detected by said first level detecting means with a preset first reference level and generating a first control signal in accordance with the level difference;
a light controlling means connected to the output of said first level comparing means for controlling the amount of light emitted from said illuminating means based on said first control signal;
a gain-variable amplifying means for receiving and amplifying the video signal from the solid state image pick-up device;
a second level detecting means connected to said gain-variable amplifying means for detecting the level of the signal therefrom; and
a circuit means connected to said second level detecting means for comparing the level of the signal detected by said second level detecting means with a preset second reference level and generating a second control signal in accordance with the level difference therebetween and providing said second control signal as a gain controlling signal to said gain-variable amplifying means.

2. The endoscope of claim 1, wherein said light controlling means comprises a diaphragm located in the optical path between said illuminating means and the subject to control the amount of light illuminating the subject, and a driver to drive and control said diaphragm on the basis of said first controlling signal.

3. The endoscope of claim 1, wherein said light controlling means comprises a polarizing filter located in the optical path between said illuminating means and the subject to control the amount of light illuminating the subject, and a driver to drive and control said polarizing filter on the basis of said first controlling signal.

4. The endoscope of claim 1, wherein said illuminating means comprises a white light source, and a rotary filter in the light path of said white light source such that said rotary filter separates the white light into 3 primary colors serially in time to provide a color period for each color.

5. The endoscope of claim 4, wherein said second level detecting means comprises:
fourth, fifth and sixth resistances connected in series and receiving the output of said gain-variable amplifying means, said fourth resistance connected to said gain-variable amplifying means and said sixth resistance connected to ground;
a second low pass filter for averaging and outputting signals corresponding to each color period, said low pass filter providing an output to said circuit means; and
an analog switch means for switching between one of three common points located between said gain-variable amplifying means and said fourth resistance, between said fourth and fifth resistances and between said fifth and sixth resistances, to provide an output to said second low pass filter in synchronization with the 3-color separation timing of said rotary filter.

6. The endoscope of claim 4, wherein said first level detecting means comprises:
first, second and third resistances connected in series between a first video signal detecting point and ground, said first video signal detecting point being positioned at a common point between the output of said solid state image pick-up device, said first level detecting means and said gain-variable amplifying means;
a low pass filter for averaging and outputting signals corresponding to each color period;
an analog switch means for switching between one of three common points located between said video signal detecting point and said first resistance, between said first and second resistances, and between said second and third resistances, to provide an output to said low pass filter, in synchronization with the 3-color separation timing of said rotary filter.

7. The endoscope of claim 6, wherein said second level detecting means comprises:
fourth, fifth and sixth resistances connected in series and receiving the output of said gain-variable amplifying means, said fourth resistance connected to said gain-variable amplifying means and said sixth resistance connected to ground;
a second low pass filter for averaging and outputting signals corresponding to each color period, said low pass filter providing an output to said circuit means; and
an analog switch means for switching between one of three common points located between said gain-variable amplifying means and said fourth resistance, between said fourth and fifth resistances and between said fifth and sixth resistances, to provide an output to said second low pass filter in synchronization with the 3-color separation timing of said rotary filter.

* * * * *